United States Patent
Zhang et al.

(10) Patent No.: US 8,962,852 B2
(45) Date of Patent: Feb. 24, 2015

(54) ASYMMETRIC HYDROGENATION METHOD FOR KETONE COMPOUND

(75) Inventors: Wanbin Zhang, Shanghai (CN); Delong Liu, Shanghai (CN); Hui Guo, Shanghai (CN); Yangang Liu, Shanghai (CN)

(73) Assignee: Nippon Chemical Industries Co., Ltd., Tokyo (JP)

( * ) Notice: Subject to any disclaimer, the term of this patent is extended or adjusted under 35 U.S.C. 154(b) by 187 days.

(21) Appl. No.: 13/447,632

(22) Filed: Apr. 16, 2012

(65) Prior Publication Data

US 2013/0053574 A1 Feb. 28, 2013

(30) Foreign Application Priority Data

Aug. 22, 2011 (CN) .......................... 2011 1 0244177

(51) Int. Cl.
| | |
|---|---|
| C07F 15/00 | (2006.01) |
| C07C 29/145 | (2006.01) |
| C07C 37/00 | (2006.01) |
| C07C 41/26 | (2006.01) |
| C07C 213/00 | (2006.01) |
| C07B 53/00 | (2006.01) |

(52) U.S. Cl.
CPC ............. *C07C 29/145* (2013.01); *C07C 37/002* (2013.01); *C07C 41/26* (2013.01); *C07C 213/00* (2013.01); *C07B 53/00* (2013.01); *C07B 2200/07* (2013.01); *C07C 2102/08* (2013.01); *C07C 2102/10* (2013.01)
USPC .......................................... 548/101; 568/814

(58) Field of Classification Search
USPC .......................................... 548/101; 568/814
See application file for complete search history.

(56) References Cited

PUBLICATIONS

Guo et al. "Efficient Ru(II)-catalyzed asymmetric hydrogenation of simple ketones with C2-symmetric planar chiral metallocenyl phosphinooxazoline ligands" Tetrahedron, 2012, vol. 68, pp. 3295-3299.*
Jiang et al. "Highly Enantioselective Hydrogenation of Simple Ketones Catalyzed by a Rh—PennPhos Complex" Angew. Chem. Int. Ed., 1998, vol. 37, pp. 1100-1103.*
Noyori et al. "Toward efficient asymmetric hydrogenation: Architectural and functional engineering of chiral molecular catalysts" PNAS, 2004, vol. 101, pp. 5356-5362.*
Liu et al. "Enantioselective transfer hydrogenation of ketones with planar chiral ruthenocene-based phosphinooxazoline ligands" Tetrahedron, 2008, vol. 64, pp. 3561-3566.*

* cited by examiner

*Primary Examiner* — Joseph Kosack
(74) *Attorney, Agent, or Firm* — Westerman, Hattori, Daniels & Adrian, LLP

(57) ABSTRACT

The invention relates to an asymmetric hydrogenation method for ketone compounds, comprising the step of: under hydrogen atmosphere, in the presence of an in situ catalyst derived from a chiral ligand and a ruthenium salt, adding a ketone compound and a base into a second solvent to carry out an asymmetric hydrogenation for the ketone compound. The invention can obtain a conversion of 100% and a highest asymmetric inducement effect of 99.7% for the ketone compound. The invention has the advantages including simple procedure, high conversion and selectivity, good atom economy and good prospect of industrial application.

11 Claims, No Drawings

ASYMMETRIC HYDROGENATION METHOD FOR KETONE COMPOUND

TECHNICAL FIELD

The invention relates to organic chemistry and drug synthesis chemistry, and in particular, relates to an asymmetric hydrogenation method for ketone compounds. The invention can provide a method for reducing a prochiral ketone to a chiral alcohol.

BACKGROUNDS

Enantiomerically pure alcohols are widely used in fine chemical industries such as pharmaceuticals, pesticides, perfumes, etc., and thus the studies on the various synthesis methods thereof have been increasing recently. The asymmetric hydrogenation of a prochiral ketone is one of the most important methods in preparing an enantiomerically pure alcohol. This method has gained much attention because of high catalytic activity, quick reaction time, good atom economy, simple product separation, simple post-processing, and less side reactions.

Based on the reasons above, numerous chiral ligands have been developed for the asymmetric hydrogenation of prochiral ketones. Among these ligands, the most representative one is BINAP-based ligands invented by Noyori, a Japanese chemist (EP0901997A1), which achieved good selectivity in the asymmetric hydrogenation of various ketone compounds. However, it is not easy to synthesize such ligand, and the costs are relatively high. In addition, the ligand cannot be stably stored. Further, many other chiral ligands have been applied to asymmetric hydrogenation of ketones. For example, Xumu Zhang et al. have mentioned that the asymmetric hydrogenation of ketones is realized by using a complex of a chiral ligand PennPhos with rhodium (Xumu Zhang et al., Highly Enantioselective Hydrogenation of Simple Ketones Catalyzed by a Rh-PennPhos Complex. Angew. Chem., Int. Ed. 1998, 37, 1100-1103). However, the selectivity of such system is not good, and the ligand is hard to be synthesized and has poor stability. In this respect, it is hard to apply this system in industrial productions. In addition, the use of metal rhodium leads to an increase of the costs.

SUMMARY OF THE INVENTION

The invention has been made through numerous researches to overcome the above-mentioned defects which existed in the prior art.

The object of the invention is to provide an asymmetric hydrogenation method for ketone compounds, which can conveniently and effectively synthesize enantiomerically pure alcohols so as to be used in various fields, such as medicine and health, fine chemical industry, and the like.

The invention overcomes the disadvantages in the prior art described above by using $C_2$-symmetric metallocenyl planar chiral ligands. The outstanding advantages of this invention are mainly as follows: (1) simple synthesis: the ligand can be obtained through only 3-4 steps with high yield; (2) stable ligand: the ligand is insensitive to water and oxygen, and thus can be stored and used easily; (3) good atom economy: since the $C_2$-symmetric planar chiral ligand has a two-center structure, one ligand molecule can coordinate with two ruthenium molecules to form two reaction centers; (4) good catalytic effect: 100% conversion with the highest stereoselectivity of 99.7% can be achieved in most ketone substrates. In view of the above, it will have an excellent industrial prospect if the $C_2$-symmetric planar chiral ligand of the invention is used in the asymmetric reduction method for ketone.

The invention has a bright prospect of industrial application, as it has the advantages including simple procedure, high conversion and selectivity, low cost, high atom economy, environment friendly, and the like.

The invention is accomplished by the following technical solutions.

The asymmetric hydrogenation method for ketone compounds of the invention comprises the step of: under hydrogen atmosphere, in the presence of an in situ catalyst derived from a chiral ligand and a ruthenium salt, adding a ketone compound and a base into a second solvent to carry out an asymmetric hydrogenation for the ketone compound.

The in situ catalyst of the invention is obtained by reacting the chiral ligand with a ruthenium salt in a first solvent.

In addition, the chiral ligand of the invention is preferably a compound of formula (IV):

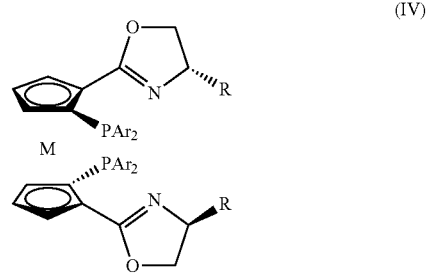

(IV)

In formula (IV), M represents Fe (iron) or Ru (ruthenium); R represents methyl, $C_2$-$C_8$ saturated aliphatic group, phenyl or benzyl; Ar represents phenyl or substituted phenyl. Preferably, in formula (IV), M represents Fe or Ru; R represents methyl, ethyl, n-propyl, i-propyl, n-butyl, s-butyl, t-butyl, pentyl, phenyl or benzyl; Ar represents phenyl, p-methylphenyl, p-methoxyphenyl, 3,5-dimethylphenyl, 3,5-di-t-butylphenyl, 3,5-di(trifluoromethyl)phenyl.

Additionally, the ruthenium salt is preferably any one selected from tris(triphenylphosphine)ruthenium(II) chloride, benzeneruthenium(II) chloride dimer, or dichloro(p-cymene)ruthenium (II) dimer.

Further, the molar ratio of Ru from ruthenium salt to the chiral ligand is preferably 1:0.5~0.7 when reacting the chiral ligand with the metal ruthenium in the first solvent to produce the in situ catalyst.

The first solvent is preferably any one selected from methanol, ethanol, i-propanol, dichloromethane, 1,4-dioxane, tetrahydrofuran, diethyl ether, toluene, or xylene.

When the chiral ligand reacts with the metal ruthenium in the first solvent to obtain the in situ catalyst, the reaction temperature is preferably 30° C.~140° C. and the reaction time is preferably 0.5 h~3 h.

The second solvent of the invention is preferably any one selected from methanol, ethanol, i-propanol, dichloromethane, 1,4-dioxane, tetrahydrofuran, diethyl ether, toluene, or xylene.

The ketone compound of the invention is preferably a compound represented by formulae (I), (II) or (III):

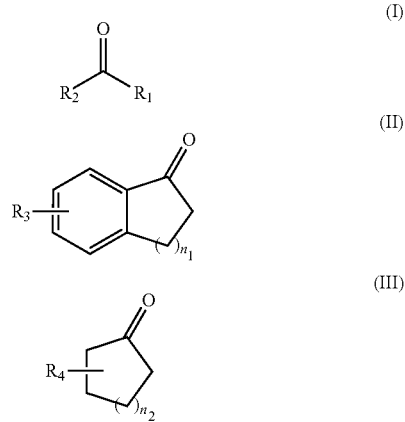

In formula (I), $R_1$ is $C_1$-$C_{15}$ linear or branched alkyl or alkenyl, or $C_3$-$C_{15}$ saturated cyclic hydrocarbyl; $R_2$ is $C_4$-$C_{20}$ substituted or unsubstituted aromatic group or aromatic heterocyclic group, or $C_1$-$C_{15}$ linear or branched alkyl or alkenyl, or $C_3$-$C_{15}$ saturated cyclic hydrocarbyl.

In formula (II) $R_3$ is $-OR_5$, $-NHR_6$, $-F$, $-Cl$, $-Br$, $-I$, $-NO_2$, $-OH$, or $C_1$-$C_5$ linear or branched alkyl or alkenyl, or $C_3$-$C_{15}$ saturated cyclic hydrocarbyl; $n_1$ is 0~4; $R_5$ and $R_6$ independently represent $C_1$-$C_{15}$ linear or branched alkyl or alkenyl, or $C_3$-$C_{15}$ saturated cyclic hydrocarbyl.

In formula (III), $R_4$ is $OR_7$—$NHR_8$, $-F$, $-Cl$, $-Br$, $-I$, $-NO_2$, $-OH$, $C_1$-$C_{15}$ linear or branched alkyl or alkenyl, or $C_3$-$C_{15}$ saturated cyclic hydrocarbyl; $n_2$ is 0~4; $R_7$ and $R_8$ independently represent $C_1$-$C_{15}$ linear or branched alkyl or alkenyl, or $C_3$-$C_{15}$ saturated cyclic hydrocarbyl.

The base of the invention is preferably any one selected from potassium t-butoxide, sodium t-butoxide, sodium ethoxide, potassium ethoxide, sodium methoxide, potassium methoxide, potassium hydroxide, sodium hydroxide, potassium carbonate, sodium carbonate, potassium bicarbonate, or sodium bicarbonate.

The molar ratio of the base to the ketone compound is preferably 0.2~0.02:1.

When the ketone compound undergoes an asymmetric hydrogenation, the reaction temperature is preferably −20~50° C., the hydrogen pressure is preferably 3~50 atm, and the reaction time is preferably 6~72 h.

Further, the invention preferably comprises the following first and second steps: in the first step, the chiral ligand reacts with ruthenium in the first solvent to obtain the in situ catalyst; in the second step, under hydrogen atmosphere, in the presence of the in situ catalyst, the ketone compound and the base are added into the second solvent to carry out the asymmetric hydrogenation for the ketone compound; and the first and second steps are continuously performed without additional separation of the in situ catalyst obtained in the first step.

DETAILED DESCRIPTION OF THE INVENTION

As described above, an asymmetric hydrogenation for ketone compounds is performed in the presence of an in situ catalyst. The in situ catalyst is a complex of ruthenium salt and chiral ligand, and the chiral ligand is a $C_2$-symmetric planar chiral ferrocenyl or ruthenoceyl ligand represented by the above formula (IV).

In formula (IV), M represents Fe or Ru; R represents methyl, $C_2$-$C_8$ saturated aliphatic group, phenyl or benzyl, and R is preferably methyl, ethyl, n-propyl, i-propyl, n-butyl, s-butyl, t-butyl, pentyl, phenyl or benzyl; Ar represents $C_4$-$C_{10}$ substituted or unsubstituted aromatic group in which the substituent group on the aromatic group can be, for example, $C_1$-$C_4$ alkyl or alkoxy or halogenated alkyl, and Ar is preferably phenyl, p-methylphenyl, p-methoxyphenyl, 3,5-dimethylphenyl, 3,5-di-t-butylphenyl, 3,5-di(trifluoromethyl)phenyl.

The ruthenium salt of the invention is preferably any one selected from tris(triphenylphosphine)ruthenium(II) chloride, benzeneruthenium(II) chloride dimer, or dichloro(p-cymene)ruthenium(II) dimer.

In the invention, when the chiral ligand reacts with ruthenium in the first solvent to obtain the in situ catalyst, the molar ratio of Ru derived from the ruthenium salt to the chiral ligand is 1:0.5~0.7, preferably 1:0.5~0.65, more preferably 1:0.5~0.6, further preferably 1:0.5~0.55.

In the invention, when the chiral ligand reacts with ruthenium in the first solvent to obtain the in situ catalyst, the reaction temperature can be set as required. However, in view of the reaction efficiency and the safety of operation, the reaction temperature is preferably 30~140° C., more preferably 40~120° C., further preferably 40~105° C., even more preferably 65~85° C.

In the invention, when the chiral ligand reacts with ruthenium in the first solvent to obtain the in situ catalyst, in view of the reaction efficiency, stirring is preferably performed. In addition, in view of both the reaction efficiency and the safety of operation, the stirring rate is preferably 200~800 rpm, more preferably 300~600 rpm, further preferably 400~500 rpm. The way of stirring can be selected arbitrarily, for example, stirring equipments with stirring paddles or magnetic stirring with a stirring bar can be employed.

In the invention, when the chiral ligand reacts with ruthenium in the first solvent to obtain the in situ catalyst, the reaction time is preferably 0.5~3 h, more preferably 1~2 h, and further preferably 1~1.5 h, in view of the yield.

Obviously, in the invention, when the chiral ligand reacts with ruthenium in the first solvent to obtain the in situ catalyst, any combination of the above-mentioned reaction temperature, stirring rate and reaction time can be employed.

In addition, the ketone compound which undergoes the asymmetric hydrogenation in the invention is a compound of formulae (I), (II) or (III) as described above. In formula (I), it is preferably that $R_1$ is methyl, ethyl, n-propyl, i-propyl, n-butyl, t-butyl, n-pentyl, n-hexyl, n-heptyl, or the like; $R_2$ is $C_4$-$C_{20}$ substituted or unsubstituted aromatic group or aromatic heterocyclic group, wherein the aromatic group can be for example, phenyl, naphthyl, anthryl, or the like; the aromatic heterocyclic group can be for example, pyridyl, furyl, thienyl, or the like; the substituent group on the aromatic group can be for example, fluoro, chloro, bromo, iodo, amine, hydroxyl, methoxy, methyl, phenyl, or the like; the aromatic group can be monosubstituted, disubstituted, or trisubstituted, and the position(s) to be substituted on the aromatic group is/are not specially limited. More specifically, the examples of the compound of formula (I) can be acetophenone, m-methylacetophenone, o-methylacetophenone, p-methylacetophenone, m-chloroacetophenone, o-chloroacetophenone, p-chloroacetophenone, m-methoxyacetophenone, o-methoxyacetophenone, p-methoxyacetophenone, p-bromoacetophenone, p-fluoroacetophenone, 3,4-dichloroacetophenone, 2,4-difluoroacetophenone, m-hydroxylacetophenone, o-hydroxylacetophenone, p-aminoacetophenone, p-phenylacetophenone, 1-acetonaphthone, 2-acetonaphthone, 3,4-dimethoxyacetophenone, 3,4,5-trimethoxyacetophenone, propiophenone, butyrophenone, i-butyrophenone, p-methyloctanophenone, 3-acetylpyridine, 2-acetylfuran, or the like.

In formula (II), it is preferably that $R_3$ is —$OCH_3$, —$NHCH_3$, —F, —Cl, —Br, —I, $NO_2$, OH, methyl, ethyl, n-propyl, i-propyl, n-butyl, i-butyl, t-butyl, or the like; $n_1$ is 1, 2, 3, or 4. More specifically, the examples of the compound of formula (II) can be 1-tetralone, 1-indanone, 5-methoxy-1-tetralone, or the like.

In formula (III), it is preferably that $R_4$ is —$OCH_3$, —$NHCH_3$, —F, —Cl, —Br, —I, $NO_2$, OH, methyl, ethyl, n-propyl, i-propyl, n-butyl, i-butyl, n-pentyl, or the like; $n_2$ is 0, 1, 2, 3, or 4. More specifically, the examples of the compound of formula (III) can be 1-methylcyclopentanone, 2-fluorocyclohexanone, 2-methoxycycloheptanone, or the like.

The base used in the invention can be an organic or inorganic base. For example, it can be alkali metal alkoxides, alkali metal hydroxides, alkali metal carbonates, or the like. More specifically, the examples of the base can be potassium t-butoxide, sodium t-butoxide, sodium ethoxide, potassium ethoxide, sodium methoxide, potassium methoxide, potassium hydroxide, sodium hydroxide, lithium hydroxide, potassium carbonate, sodium carbonate, potassium bicarbonate or sodium bicarbonate.

In the invention, when the ketone compound undergoes the asymmetric hydrogenation, the molar ratio of the base and the ketone compound can be 0.2~0.02:1, preferably 0.15~0.03:1, more preferably 0.15~0.04:1, further preferably 0.1~0.06:1, and even more preferably 0.1~0.08:1.

In the invention, when the ketone compound undergoes the asymmetric hydrogenation, the molar ratio of the ketone compound to the in situ catalyst can be 100~5000:1. Actually, there is no limitation to the molar ratio of the ketone to the in situ catalyst, because the in situ catalyst has such a high catalytic efficiency that the asymmetric hydrogenation for ketone can be performed even with little amount of in situ catalyst, and a very high conversion and very good inducement effect can be obtained. This can also be confirmed by the Examples below.

In the invention, when the ketone compound undergoes the asymmetric hydrogenation, the reaction temperature can be set as required. However, in view of the reaction efficiency and the safety of operation, the reaction temperature is −20~50° C., preferably −10~40° C., more preferably −10~25° C., further preferably 0~20° C., and even more preferably 10~20° C.

In the invention, when the ketone compound undergoes the asymmetric hydrogenation, in view of the reaction efficiency, stirring is preferably performed. In addition, in view of both the reaction efficiency and the safety of operation, the stirring rate is preferably 200~800 rpm, more preferably 300~600 rpm, further preferably 400~500 rpm. The way of stirring can be selected arbitrarily, for example, stirring equipments with stirring paddles or magnetic stirring with a stirring bar can be employed.

In the invention, when the ketone compound undergoes the asymmetric hydrogenation, there is no limitation to the reaction time. However, the reaction time is preferably 6~72 h, more preferably 12~48 h, further preferably 12~24 h, and even more preferably 18~24 h, in view of the yield.

In the invention when the ketone compound undergoes the asymmetric hydrogenation, there is no limitation to the hydrogen pressure. However, in view of the yield, the pressure is preferably 3~50 atm, more preferably 5~40 atm, further preferably 10~20 atm, and even more preferably 10~15 atm.

Obviously, when the ketone compound undergoes the asymmetric hydrogenation in the invention, any combination of the above-mentioned reaction temperature, stirring rate, reaction time and hydrogen pressure can be employed Further, in the invention, when the chiral ligand reacts with ruthenium in the first solvent to obtain the in situ catalyst and when the ketone compound undergoes the asymmetric hydrogenation, stirring under heat is preferred to reduce the reaction time and improve the reaction efficiency.

The first and second solvents in the invention can be the same or different. However, the first and second solvents are preferred to be the same in view of simple operation.

The invention preferably comprises the following first and second steps. In the first step, the chiral ligand reacts with the ruthenium salt in the first solvent to obtain the in situ catalyst; in the second step, under hydrogen atmosphere, in the presence of the in situ catalyst obtained from the chiral ligand and ruthenium, the ketone compound and the base are added into the second solvent to carry out the asymmetric hydrogenation for the ketone compound; and the first and second steps are continuously performed without additional separation of the in situ catalyst obtained in the first step.

EXAMPLES

The examples of the invention will be described in detail hereinafter. It is noted that the examples are carried out based on the technical solutions of the invention. Although detailed embodiments and specific procedures are provided, the invention is not limited to these examples.

The "mol %" used in the following examples refers to the molar percentage of a substance relative to a ketone compound.

Example 1

Preparation of 1-phenethanol from acetophenone

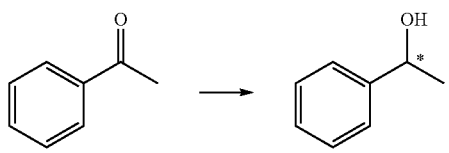

Tris(triphenylphosphine)ruthenium(II) chloride (3.8 mg, 4 μmol, 1 mol %) and a chiral ligand (M=Ru, R=i-Pr, Ar=4-MeC$_6$H$_4$—, 2.6 μmol, 0.65 mol %) were dissolved in methanol (3 mL) under nitrogen atmosphere, and then heated and stirred for 2 h at 65° C. After the mixture was cooled to room temperature, acetophenone (0.4 mmol), methane (2 mL), and a solution of sodium hydroxide in methane (0.4 mL, 0.2 M) were added thereto. The reaction system was placed in an autoclave, and stirred for 12 h under H$_2$ (10 atm) at 10° C. The solvent was removed under reduced pressure, and the resultants were separated by column chromatography (silica gel column; eluent: ethyl acetate/petroleum ether=1/5). Accordingly, pure 1-phenethanol was obtained and the ee value (ee=97%) was measured by GC analysis.

Example 2

Preparation of 1-phenethanol from acetophenone

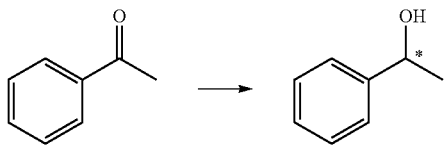

Tris(triphenylphosphine)ruthenium(II) chloride (3.8 mg, 4 μmol, 1 mol %) and a chiral ligand (M=Ru, R=s-Bu, Ar=C$_6$H$_5$—, 2.6 μmol, 0.65 mol %) were dissolved in ethanol (3 mL) under nitrogen atmosphere, and then heated and stirred for 2 h at 80° C. After the mixture was cooled to room temperature, acetophenone (0.4 mmol), ethanol (2 mL), and a solution of sodium hydroxide in ethane (0.4 mL, 0.2 M) were added thereto. The reaction system was placed in an autoclave, and stirred for 12 h under H$_2$ (20 atm) at 10° C. The solvent was removed under reduced pressure, and the resultants were separated by column chromatography (silica gel column; eluent: ethyl acetate/petroleum ether=1/5). Accordingly, pure 1-phenethanol was obtained and the ee value (ee=99.0%) was measured by GC analysis.

Example 3

Preparation of 1-phenethanol from acetophenone

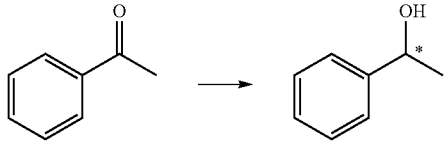

Tris(triphenylphosphine)ruthenium(II) chloride (3.8 mg, 4 μmol, 1 mol %) and a chiral ligand (M=Fe, R=Me, Ar=3,5-(CF$_3$)$_2$C$_6$H$_3$—, 2.6 μmol, 0.65 mol %) were dissolved in toluene (3 mL) under nitrogen atmosphere, and then heated and stirred for 2 h at 120° C. After the mixture was cooled to room temperature, acetophenone (0.4 mmol), toluene (2 mL), and an aqueous solution of potassium hydroxide (0.4 mL, 0.2 M) were added thereto. The reaction system was placed in an autoclave, and stirred for 12 h under H$_2$ (20 atm) at 10° C. The solvent was removed under reduced pressure, and the resultants were separated by column chromatography (silica gel column; eluent:ethyl acetate/petroleum ether=1/5). Accordingly, pure 1-phenethanol was obtained and the ee value (ee=99.3%) was measured by GC analysis.

Example 4

Preparation of 1-phenethanol from acetophenone

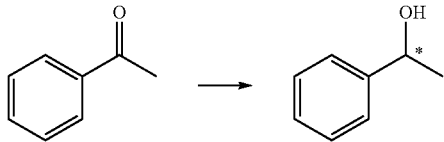

Tris(triphenylphosphine)ruthenium(II) chloride (1.9 mg, 2 μmol, 0.5 mol %) and a chiral ligand (M=Fe, R=n-Pr, Ar=3,5-t-Bu$_2$C$_6$H$_3$—, 1.3 μmol, 0.33 mol %) were dissolved in tetrahydrofuran (3 mL) under nitrogen atmosphere, and then heated and stirred for 1 h at 65° C. After the mixture was cooled to room temperature, acetophenone (0.4 mmol), tetrahydrofuran (2 mL), an aqueous solution of potassium carbonate (0.2 mL, 0.2 M) were added thereto. Thereafter, the reaction system was placed in an autoclave, and stirred for 48 h under H$_2$ (20 atm) at 0° C. The solvent was removed under reduced pressure, and the resultants were separated by column chromatography (silica gel column; eluent: ethyl acetate/petroleum ether=1/5). Accordingly, pure 1-phenethanol was obtained and the ee value (ee=97%) was measured by GC analysis.

Example 5

Preparation of 1-phenethanol from acetophenone

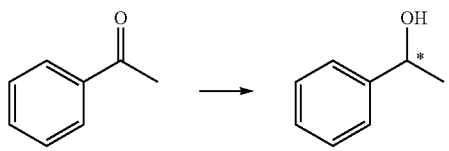

Tris(triphenylphosphine)ruthenium(II) chloride (3.8 mg, 4 μmol, 1 mol %) and a chiral ligand (M=Fe, R=Bn, Ar=C$_6$H$_5$—, 2.6 μmol, 0.65 mol %) were dissolved in i-propanol (3 mL) under nitrogen atmosphere, and then heated and stirred for 2 h at 85° C. After the mixture was cooled to room temperature, acetophenone (0.4 mmol), i-propanol (2 mL) and a solution of potassium t-butoxide in i-propanol (0.4 mL, 0.2 M) were added thereto. Thereafter, the reaction system was placed in an autoclave, and stirred for 12 h under H$_2$ (20 atm) at 10° C. The solvent was removed under reduced pressure, and the resultants were separated by column chromatography (silica gel column; eluent: ethyl acetate/petroleum ether=1/5). Accordingly, pure 1-phenethanol was obtained and the ee value (ee=99.1%) was measured by GC analysis.

Example 6

Preparation of 1-phenethanol from acetophenone

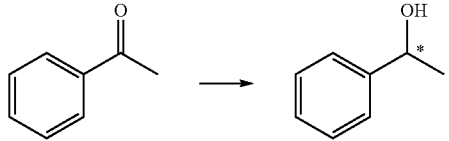

Benzeneruthenium(II) chloride dimer (0.5 mg, 1 μmol, 0.25 mol %) and a chiral ligand (M=Fe, R=Ph, Ar=4-MeOC$_6$H$_4$—, 2.6 μmol, 0.33 mol %) were dissolved in ether (3 mL) under nitrogen atmosphere, and then heated and stirred for 2 h at 40° C. After the mixture was cooled to room temperature, acetophenone (0.8 mmol), ether (2 mL) and an aqueous solution of sodium carbonate (0.4 mL, 0.2 M) were added thereto. Thereafter, the reaction system was placed in an autoclave, and stirred for 6 h under H$_2$ (40 atm) at 50° C. The solvent was removed under reduced pressure, and the resultants were separated by column chromatography (silica gel column; eluent:ethyl acetate/petroleum ether=1/5). Accordingly, pure 1-phenethanol was obtained and the ee value (ee=98%) was measured by GC analysis.

Example 7

Preparation of 1-phenethanol from acetophenone

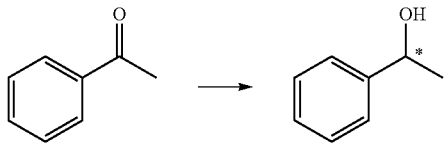

Tris(triphenylphosphine)ruthenium(II) chloride (3.8 mg, 4 μmol, 1 mol %) and a chiral ligand (M=Ru, R=i-Pr, Ar=C$_6$H$_5$—, 2.6 μmol, 0.65 mol %) were dissolved in tetrahydrofuran (3 mL) under nitrogen atmosphere, and then heated and stirred for 2 h at 65° C. After the mixture was cooled to room temperature, acetophenone (0.4 mmol), tetrahydrofuran (2 mL) and a solution of sodium ethoxide in tetrahydrofuran (0.4 mL, 0.2 M) were added thereto. Thereafter, the reaction system was placed in an autoclave, and stirred for 12 h under H$_2$ (10 atm) at 10° C. The solvent was removed under reduced pressure, and the resultants were separated by column chromatography (silica gel column; eluent: ethyl acetate/petroleum ether=1/5). Accordingly, pure 1-phenethanol was obtained and the ee value (ee=98%) was measured by GC analysis.

Example 8

Preparation of 1-phenethanol from acetophenone

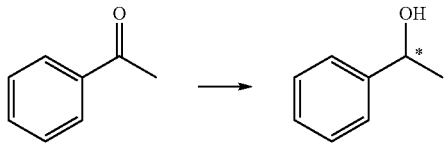

Dichloro(p-cymene)ruthenium(II) dimer (1.2 mg, 2 μmol, 0.5 mol %) and a chiral ligand (M=Ru, R=t-Bu, Ar=3,5-Me$_2$C$_6$H$_3$—, 2.6 μmol, 0.65 mol %) were dissolved in i-propanol (3 mL) under nitrogen atmosphere, and then heated and stirred for 0.5 h at 85° C. After the mixture was cooled to room temperature, acetophenone (0.4 mmol), i-propanol (2 mL) and a solution of sodium ethoxide in i-propanol (0.8 mL, 0.2 M) were added thereto. Thereafter, the reaction system was placed in an autoclave, and stirred for 6 h under H$_2$ (10 atm) at 25° C. The solvent was removed under reduced pressure, and the resultants were separated by column chromatography (silica gel column; eluent: ethyl acetate/petroleum ether=1/5). Accordingly, pure 1-phenethanol was obtained and the ee value (ee=99.1%) was measured by GC analysis.

Example 9

Preparation of 1-(m-methylphenyl)ethanol from m-methyl acetophenone

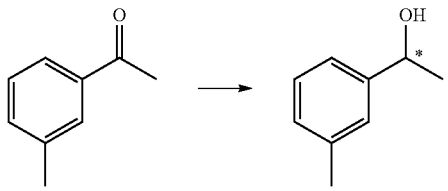

Tris(triphenylphosphine)ruthenium(II) chloride (3.8 mg, 4 μmol, 1 mol %) and a chiral ligand (M=Ru, R=i-Pr, Ar=C$_6$H$_5$—, 2.6 μmol, 0.65 mol %) were dissolved in dichloromethane (3 mL) under nitrogen atmosphere, and then heated and stirred for 0.5 h at 40° C. After the mixture was cooled to room temperature, m-methylacetophenone (0.4 mmol), dichloromethane (2 mL) and an aqueous solution of lithium hydroxide (0.4 mL, 0.2 M) were added thereto. Thereafter, the reaction system was placed in an autoclave, and stirred for 24 h under H$_2$ (20 atm) at 0° C. The solvent was removed under reduced pressure, and the resultants were separated by column chromatography (silica gel column; eluent: ethyl acetate/petroleum ether=1/5). Accordingly, pure 1-(m-methylphenyl)ethanol was obtained and the ee value (ee=99.0%) was measured by GC analysis.

Example 10

Preparation of 1-(o-methylphenyl)ethanol from o-methyl acetophenone

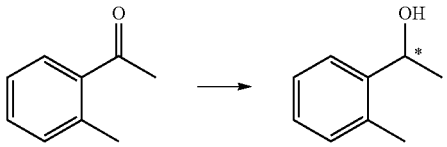

Dichloro(p-cymene)ruthenium(II) dimer (1.2 mg, 2 μmol, 0.5 mol %) and a chiral ligand (M=Fe, R=i-Pr, Ar=C$_6$H$_5$—, 2.6 μmol, 0.65 mol %) were dissolved in toluene (3 mL) under nitrogen atmosphere, and then heated and stirred for 2 h at 120° C. After the mixture was cooled to room temperature, o-methylacetophenone (0.4 mmol), toluene (2 mL) and an aqueous solution of potassium hydroxide (0.4 mL, 0.2 M) were added thereto. Thereafter, the reaction system was placed in an autoclave, and stirred for 24 h under H$_2$ (10 atm) at 25° C. The solvent was removed under reduced pressure, and the resultants were separated by column chromatography (silica gel column; eluent:ethyl acetate/petroleum ether=1/5). Accordingly, pure 1-(o-methylphenyl)ethanol was obtained and the ee value (ee=98%) was measured by GC analysis.

Example 11

Preparation of 1-(p-methylphenyl)ethanol from p-methyl acetophenone

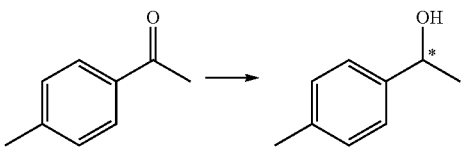

Tris(triphenylphosphine)ruthenium(II) chloride (3.8 mg, 4 μmol, 0.5 mol %) and a chiral ligand (M=Ru, R=t-Bu, Ar=C$_6$H$_5$—, 2.6 μmol, 0.33 mol %) were dissolved in ether (3 mL) under nitrogen atmosphere, and then heated and stirred for 1 h at 40° C. After the mixture was cooled to room temperature, p-methylacetophenone (0.8 mmol), ether (2 mL) and a solution of potassium ethoxide in i-propanol (0.4 mL, 0.2 M) were added thereto. Thereafter, the reaction system was placed in an autoclave, and stirred for 12 h under H$_2$ (10 atm) at 25° C. The solvent was removed under reduced pressure, and the resultants were separated by column chromatography (silica gel column; eluent:ethyl acetate/petro-

Example 12

Preparation of 1-(m-chlorophenyl)ethanol from m-chloro acetophenone

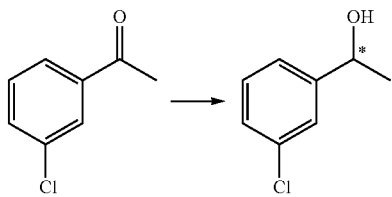

Tris(triphenylphosphine)ruthenium (II) chloride (3.8 mg, 4 μmol, 0.5 mol %) and a chiral ligand (M=Fe, R=t-Bu, Ar=C_6H_5—, 2.6 μmol, 0.33 mol %) were dissolved in i-propanol (3 mL) under nitrogen atmosphere, and then heated and stirred for 1 h at 85° C. After the mixture was cooled to room temperature, m-chloroacetophenone (0.8 mmol), i-propanol (2 mL) and a solution of potassium methoxide in i-propanol (0.4 mL, 0.2 M) were added thereto. Thereafter, the reaction system was placed in an autoclave, and stirred for 24 h under $H_2$ (50 atm) at 10° C. The solvent was removed under reduced pressure, the resultants were separated by column chromatography (silica gel column; eluent:ethyl acetate/petroleum ether=1/5). Accordingly, pure 1-(m-chlorophenyl)ethanol was obtained and the ee value (ee=98%) was measured by GC analysis.

Example 13

Preparation of 1-(o-chlorophenyl)ethanol from o-chloro acetophenone

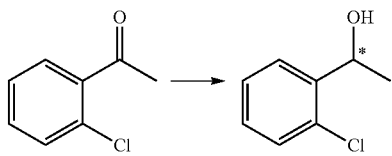

Benzeneruthenium(II) chloride dimer (0.5 mg, 1 μmol, 0.25 mol %) and a chiral ligand (M=Ru, R=t-Bu, Ar=C_6H_5—, 2.6 μmol, 0.33 mol %) were dissolved in methanol (3 mL) under nitrogen atmosphere, and then heated and stirred for 2 h at 65° C. After the mixture was cooled to room temperature, o-chloroacetophenone (0.8 mmol), methanol (2 mL) and a solution of sodium t-butoxide in methanol (0.4 mL, 0.2 M) were added thereto. Thereafter, the reaction system was placed in an autoclave, and stirred for 6 h under $H_2$ (40 atm) at 50° C. The solvent was removed under reduced pressure, and the resultants were separated by column chromatography (silica gel column; eluent:ethyl acetate/petroleum ether=1/5). Accordingly, pure 1-(o-chlorophenyl)ethanol was obtained and the ee value (ee=97%) was measured by GC analysis.

Example 14

Preparation of 1-(p-chlorophenyl)ethanol from p-chloro acetophenone

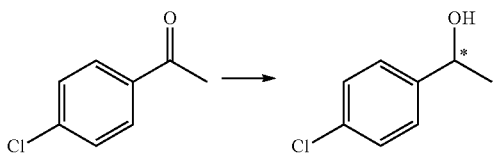

Tris(triphenylphosphine)ruthenium(II) chloride (3.8 mg, 4 μmol, 1 mol %) and a chiral ligand (M=Fe, R=n-Pr, Ar=C_6H_5—, 2.6 μmol, 0.65 mol %) were dissolved in ethanol (3 mL) under nitrogen atmosphere, and then heated and stirred for 2 h at 80° C. After the mixture was cooled to room temperature, p-chloroacetophenone (0.4 mmol), ethanol (2 mL) and a solution of sodium ethoxide in ethanol (0.2 mL, 0.2 M) were added thereto. Thereafter, the reaction system was placed in an autoclave, and stirred for 24 h under $H_2$ (5 atm) at 0° C. The solvent was removed under reduced pressure, the resultants were separated by column chromatography (silica gel column; eluent: ethyl acetate/petroleum ether=1/5). Accordingly, pure 1-(p-chlorophenyl)ethanol was obtained and the ee value (ee=97%) was measured by GC analysis.

Example 15

Preparation of m-methoxyphenylethanol from m-methoxyacetophenone

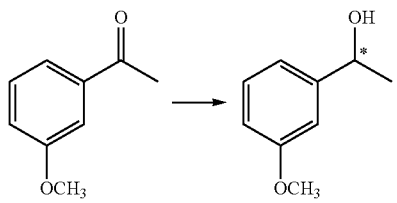

Tris(triphenylphosphine)ruthenium(II) chloride (3.8 mg, 4 μmol, 1 mol %) and a chiral ligand (M=Ru, R=t-Bu, Ar=C_6H_5—, 2.6 μmol, 0.65 mol %) were dissolved in i-propanol (3 mL) under nitrogen atmosphere, and then heated and stirred for 0.5 h at 85° C. After the mixture was cooled to room temperature, m-methoxyacetophenone (0.4 mmol), i-propanol (2 mL) and a solution of sodium methoxide in i-propanol (0.4 mL, 0.2 M) were added thereto. Thereafter, the reaction system was placed in an autoclave, and stirred for 6 h under $H_2$ (5 atm) at 40° C. The solvent was removed under reduced pressure, and the resultants were separated by column chromatography (silica gel column; eluent:ethyl acetate/petroleum ether=1/5). Accordingly, pure m-methoxyphenylethanol was obtained and the ee value (ee=99.2%) was measured by GC analysis.

Example 16

Preparation of 1-(o-methoxyphenyl)ethanol from o-methoxyacetophenone

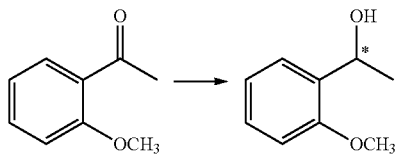

Benzeneruthenium(II) chloride dimer (1.0 mg, 2 μmol, 0.5 mol %) and a chiral ligand (M=Ru, R=t-Bu, Ar=$C_6H_5$—, 2.6 μmol, 0.65 mol %) were dissolved in xylene (3 mL) under nitrogen atmosphere, and then heated and stirred for 1 h at 140° C. After the mixture was cooled to room temperature, o-methoxyacetophenone (0.4 mmol), xylene (2 mL) and an aqueous solution of potassium hydroxide (0.4 mL, 0.2 M) were added thereto. Thereafter, the reaction system was placed in an autoclave, and stirred for 12 h under $H_2$ (3 atm) at 25° C. The solvent was removed under reduced pressure, and the resultants were separated by column chromatography (silica gel column; eluent: ethyl acetate/petroleum ether=1/5). Accordingly, pure (o-methoxyphenyl)ethanol was obtained and the ee value (ee=98%) was measured by GC analysis.

Example 17

Preparation of 1-(p-methoxyphenyl)ethanol from p-methoxyacetophenone

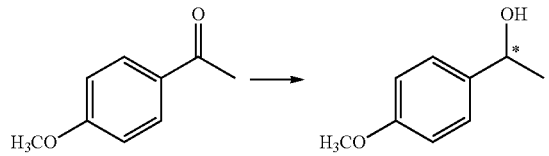

Tris(triphenylphosphine)ruthenium(II) chloride (1.9 mg, 2 μmol, 0.5 mol %) and a chiral ligand (M=Fe, R=i-Pr, Ar=3,5-$Me_2C_6H_3$—, 1.3 μmol, 0.33 mol %) were dissolved in tetrahydrofuran (3 mL) under nitrogen atmosphere, and then heated and stirred for 1 h at 65° C. After the mixture was cooled to room temperature, p-methoxyacetophenone (0.4 mmol), tetrahydrofuran (2 mL) and an aqueous solution of sodium bicarbonate (0.4 mL, 0.2 M) were added thereto. Thereafter, the reaction system was placed in an autoclave, and stirred for 12 h under $H_2$ (20 atm) at 40° C. The solvent was removed under reduced pressure, and the resultants were separated by column chromatography (silica gel column; eluent: ethyl acetate/petroleum ether=1/5). Accordingly, pure 1-(p-methoxyphenyl)ethanol was obtained and the ee value (ee=99.1%) was measured by GC analysis.

Example 18

Preparation of 1-(p-bromophenyl)ethanol from p-bromoacetophenone

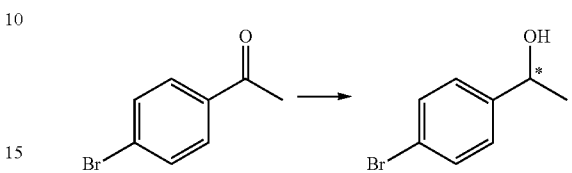

Tris(triphenylphosphine)ruthenium(II) chloride (3.8 mg, 4 μmol, 1 mol %) and a chiral ligand (M=Ru, R=n-Pr, Ar=$C_6H_5$—, 2.6 μmol, 0.65 mol %) were dissolved in ethanol (3 mL) under nitrogen atmosphere, and then heated and stirred for 1 h at 80° C. After the mixture was cooled to room temperature, p-bromoacetophenone (0.4 mmol), ethanol (2 mL) and a solution of sodium methoxide in ethanol (0.8 mL, 0.2 M) were added thereto. Thereafter, the reaction system was placed in an autoclave, and stirred for 12 h under $H_2$ (10 atm) at 25° C. The solvent was removed under reduced pressure, and the resultants were separated by column chromatography (silica gel column; eluent:ethyl acetate/petroleum ether=1/5). Accordingly, pure 1-(p-bromophenyl)ethanol was obtained and the ee value (ee=97%) was measured by GC analysis.

Example 19

Preparation of 1-(p-fluorophenyl)ethanol from p-fluoroacetophenone

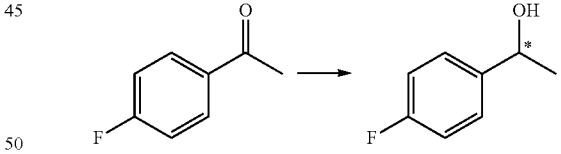

Dichloro(p-cymene)ruthenium(II) dimer (1.2 mg, 2 μmol, 0.5 mol %) and a chiral ligand (M=Ru, R=i-Pr, Ar=$C_6H_5$—, 2.6 μmol, 0.65 mol %) were dissolved in 1,4-dioxane (3 mL) under nitrogen atmosphere, and then heated and stirred for 1 h at 105° C. After the mixture was cooled to room temperature, p-fluoroacetophenone (0.4 mmol), 1,4-dioxane (2 mL) and a solution of sodium carbonate in 1,4-dioxane (0.8 mL, 0.2 M) were added thereto. Thereafter, the reaction system was placed in an autoclave, and stirred for 24 h under $H_2$ (5 atm) at 10° C. The solvent was removed under reduced pressure, and the resultants were separated by column chromatography (silica gel column; eluent: ethyl acetate/petroleum ether=1/5). Accordingly, pure 1-(p-fluorophenyl)ethanol was obtained and the ee value (ee=98%) was measured by GC analysis.

Example 20

Preparation of 1-(3,4-dichlorophenyl)ethanol from 3,4-dichloroacetophenone

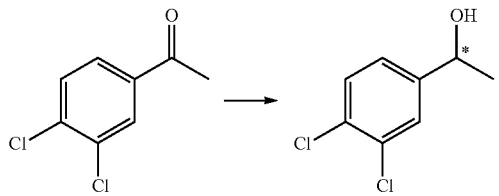

Benzeneruthenium(II) chloride dimer (1.0 mg, 2 μmol, 0.5 mol %) and a chiral ligand (M=Fe, R=s-Bu, Ar=$C_6H_5$—, 2.6 μmol, 0.65 mol %) were dissolved in i-propanol (3 mL) under nitrogen atmosphere, and then heated and stirred for 0.5 h at 85° C. After the mixture was cooled to room temperature, 3,4-dichloroacetophenone (0.4 mmol), i-propanol (3 mL) and a solution of potassium t-butoxide in i-propanol (0.4 mL, 0.2 M) were added thereto. Thereafter, the reaction system was placed in an autoclave, and stirred for 72 h under $H_2$ (3 atm) at −20° C. The solvent was removed under reduced pressure, and the resultants were separated by column chromatography (silica gel column; eluent: ethyl acetate/petroleum ether=1/5). Accordingly, pure 1-(3,4-dichlorophenyl)ethanol was obtained and the ee value (ee=95%) was measured by GC analysis.

Example 21

Preparation of 1-(2,4-difluorophenyl)ethanol from 2,4-difluoroacetophenone

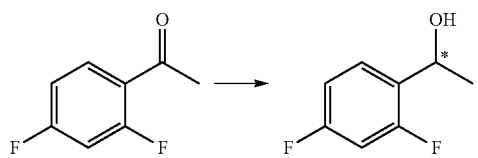

Dichloro(p-cymene)ruthenium(II) dimer (1.2 mg, 2 μmol, 0.5 mol %) and a chiral ligand (M=Ru, R=t-Bu, Ar=$C_6H_5$—, 2.6 μmol, 0.65 mol %) were dissolved in i-propanol (3 mL) under nitrogen atmosphere, and then heated and stirred for 1 h at 85° C. After the mixture was cooled to room temperature, 2,4-difluoroacetophenone (0.4 mmol), i-propanol (2 mL) and an aqueous solution of sodium hydroxide (1.0 mL, 0.2 M) were added thereto. Thereafter, the reaction system was placed in an autoclave, and stirred for 24 h under $H_2$ (20 atm) at 0° C. The solvent was removed under reduced pressure, and the resultants were separated by column chromatography (silica gel column; eluent:ethyl acetate/petroleum ether=1/5). Accordingly, pure 1-(2,4-difluorophenyl)ethanol was obtained and the ee value (ee=93%) was measured by GC analysis.

Example 22

Preparation of 1-(m-hydroxylphenyl)ethanol from m-hydroxyacetophenone

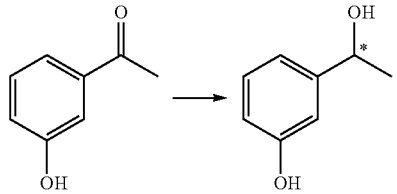

Dichloro(p-cymene)ruthenium(II) dimer (1.2 mg, 2 μmol, 0.5 mol %) and a chiral ligand (M=Ru, R=Bn, Ar=3,5-$Me_2C_6H_3$—, 2.6 μmol, 0.65 mol %) were dissolved in i-propanol (3 mL) under nitrogen atmosphere, and then heated and stirred for 0.5 h at 85° C. After the mixture was cooled to room temperature, m-hydroxyacetophenone (0.4 mmol), i-propanol (2 mL) and a solution of sodium ethoxide in i-propanol (0.4 mL, 0.2M) were added thereto. Thereafter, the reaction system was placed in an autoclave, and stirred for 6 h under $H_2$ (50 atm) at 25° C. The solvent was removed under reduced pressure, and the resultants were separated by column chromatography (silica gel column; eluent: ethyl acetate/petroleum ether=1/2). Accordingly, pure 1-(m-hydroxylphenyl)ethanol was obtained and the ee value (ee=98%) was measured by GC analysis.

Example 23

Preparation of 1-(o-hydroxylphenyl)ethanol from o-hydroxyacetophenone

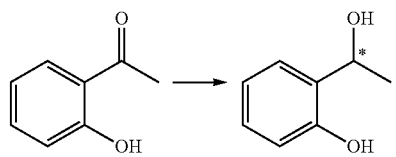

Tris(triphenylphosphine)ruthenium (II) chloride (1.9 mg, 2 μmol, 0.5 mol %) and a chiral ligand (M=Ru, R=Ph, Ar=$C_6H_5$—, 1.3 μmol, 0.33 mol %) were dissolved in xylene (3 mL) under nitrogen atmosphere, and then heated and stirred for 1 h at 140° C. After the mixture was cooled to room temperature, o-hydroxyacetophenone (0.4 mmol), xylene (2 mL) and an aqueous solution of sodium hydroxide (0.4 mL, 0.2 M) were added thereto. Thereafter, the reaction system was placed in an autoclave, and stirred for 12 h under $H_2$ (10 atm) at 25° C. The solvent was removed under reduced pressure, and the resultants were separated by column chromatography (silica gel column; eluent:ethyl acetate/petroleum ether=1/2). Accordingly, pure 1-(o-hydroxylphenyl)ethanol was obtained and the ee value (ee=97%) was measured by GC analysis.

Example 24

Preparation of 1-(p-aminophenyl)ethanol from p-amino-acetophenone

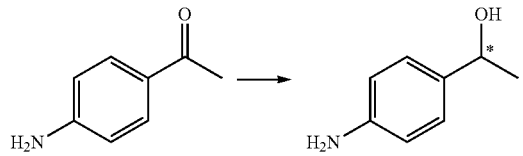

Tris(triphenylphosphine)ruthenium(II) chloride (1.9 mg, 2 μmol, 0.5 mol %) and a chiral ligand (M=Fe, R=t-Bu, Ar=3,5-(CF$_3$)$_2$C$_6$H$_3$—, 1.3 μmol, 0.33 mol %) were dissolved in tetrahydrofuran (3 mL) under nitrogen atmosphere, and then heated and stirred for 1 h at 65° C. After the mixture was cooled to room temperature, p-amino-acetophenone (0.4 mmol), tetrahydrofuran (2 mL) and an aqueous solution of sodium carbonate (0.4 mL, 0.2 M) were added thereto. Thereafter, the reaction system was placed in an autoclave, and stirred for 48 h under H$_2$ (20 atm) at 0° C. The solvent was removed under reduced pressure, and the resultants were separated by column chromatography (silica gel column; eluent:ethyl acetate/petroleum ether=1/1). Accordingly, pure 1-(p-aminophenyl)ethanol was obtained and the ee value (ee=97%) was measured by GC analysis.

Example 25

Preparation of 1-(p-phenylphenyl)ethanol from p-phenyl-acetophenone

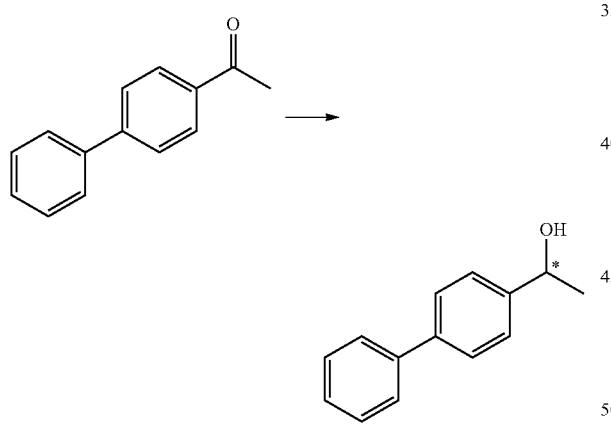

Tris(triphenylphosphine)ruthenium (II) chloride (1.9 mg, 2 μmol, 0.5 mol %) and a chiral ligand (M=Ru, R=i-Pr, Ar=C$_6$H$_5$—, 1.3 μmol, 0.33 mol %) were dissolved in i-propanol (3 mL) under nitrogen atmosphere, and then heated and stirred for 1 h at 85° C. After the mixture was cooled to room temperature, p-phenyl-acetophenone (0.8 mmol), i-propanol (2 mL) and a solution of potassium carbonate in i-propanol (0.8 mL, 0.2 M) were added thereto. Thereafter, the reaction system was placed in an autoclave, and stirred for 24 h under H$_2$ (10 atm) at −20° C. The solvent was removed under reduced pressure, and the resultants were separated by column chromatography (silica gel column; eluent: ethyl acetate/petroleum ether=1/5). Accordingly, pure 1-(p-phenylphenyl)ethanol was obtained and the ee value (ee=99.2%) was measured by GC analysis.

Example 26

Preparation of 1-(1-naphthyl)ethanol from 1-acetonaphthone

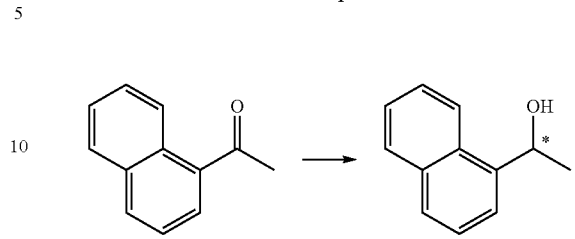

Tris(triphenylphosphine)ruthenium(II) chloride (3.8 mg, 4 μmol, 1 mol %) and a chiral ligand (M=Fe, R=Me, Ar=C$_6$H$_5$—, 2.6 μmol, 0.65 mol %) were dissolved in 1,4-dioxane (3 mL) under nitrogen atmosphere, and then heated and stirred for 2 h at 105° C. After the mixture was cooled to room temperature, 1-acetonaphthone (0.4 mmol), 1,4-dioxane (2 mL) and a solution of potassium t-butoxide in 1,4-dioxane (0.4 mL, 0.4 M) were added thereto. Thereafter, the reaction system was placed in an autoclave, and stirred for 24 h under H$_2$ (40 atm) at 0° C. The solvent was removed under reduced pressure, and the resultants were separated by column chromatography (silica gel column; eluent: ethyl acetate/petroleum ether=1/5). Accordingly, pure 1-(1-naphthyl)ethanol was obtained and the ee value (ee=98%) was measured by GC analysis.

Example 27

Preparation of 1-(2-naphthyl)ethanol from 2-acetonaphthone

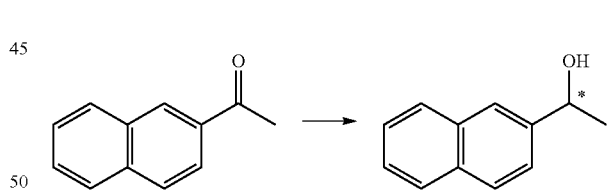

Tris(triphenylphosphine)ruthenium(II) chloride (3.8 mg, 4 μmol, 1 mol %) and a chiral ligand (M=Ru, R=t-Bu, Ar=3,5-t-Bu$_2$C$_6$H$_3$—, 2.6 μmol, 0.65 mol %) were dissolved in dichloromethane (3 mL) under nitrogen atmosphere, and then heated and stirred for 0.5 h at 40° C. After the mixture was cooled to room temperature, 2-acetonaphthone (0.4 mmol), dichloromethane (2 mL) and an aqueous solution of potassium hydroxide (0.2 mL, 0.2 M) were added thereto. Thereafter, the reaction system was placed in an autoclave, and stirred for 24 h under H$_2$ (10 atm) at 50° C. The solvent was removed under reduced pressure, and the resultants were separated by column chromatography (silica gel column; eluent: ethyl acetate/petroleum ether=1/5). Accordingly, pure 1-(2-naphthyl)ethanol was obtained and the ee value (ee=98%) was measured by GC analysis.

Example 28

Preparation of 1-(3,4-dimethoxyphenyl)ethanol from 3,4-dimethoxyacetophenone

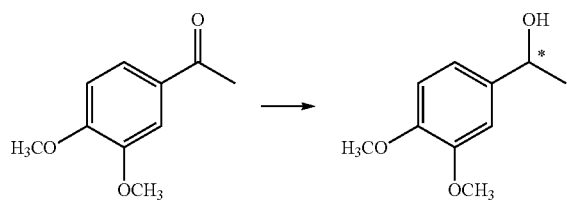

Tris(triphenylphosphine)ruthenium(II) chloride (0.38 mg, 0.4 μmol, 0.1 mol %) and a chiral ligand (M=Fe, R=t-Bu, Ar=C₆H₅—, 0.26 μmol, 0.065 mol %) were dissolved in toluene (3 mL) under nitrogen atmosphere, and then heated and stirred for 1 h at 120° C. After the mixture was cooled to room temperature, 3,4-dimethoxyacetophenone (0.4 mmol), toluene (2 mL) and an aqueous solution of sodium carbonate (0.4 mL, 0.2 M) were added thereto. Thereafter, the reaction system was placed in an autoclave, and stirred for 24 h under $H_2$ (10 atm) at 25° C. The solvent was removed under reduced pressure, and the resultants were separated by column chromatography (silica gel column; eluent: ethyl acetate/petroleum ether=1/5). Accordingly, pure 1-(3,4-dimethoxyphenyl)ethanol was obtained and the ee value (ee=96%) was measured by GC analysis.

Example 29

Preparation of 1-(3,4,5-trimethoxyphenyl)ethanol from 3,4,5-trimethoxyacetophenone

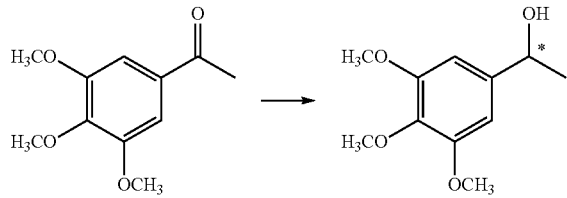

Tris(triphenylphosphine)ruthenium(II) chloride (3.8 mg, 4 μmol, 1 mol %) and a chiral ligand (M=Ru, R=i-Pr, Ar=C₆H₅—, 2.6 μmol, 0.65 mol %) were dissolved in ethanol (3 mL) under nitrogen atmosphere, and then heated and stirred for 1 h at 80° C. After the mixture was cooled to room temperature, 3,4,5-trimethoxyacetophenone (0.4 mmol), ethanol (2 mL) and a solution of sodium t-butoxide in ethanol (0.4 mL, 0.2 M) were added thereto. Thereafter, the reaction system was placed in an autoclave, and stirred for 48 h under $H_2$ (10 atm) at 0° C. The solvent was removed under reduced pressure, and the resultants were separated by column chromatography (silica gel column; eluent:ethyl acetate/petroleum ether=1/5). Accordingly, pure 1-(3,4,5-trimethoxyphenyl)ethanol was obtained and the ee value (ee=97%) was measured by GC analysis.

Example 30

Preparation of 1-phenylpropanol from propiophenone

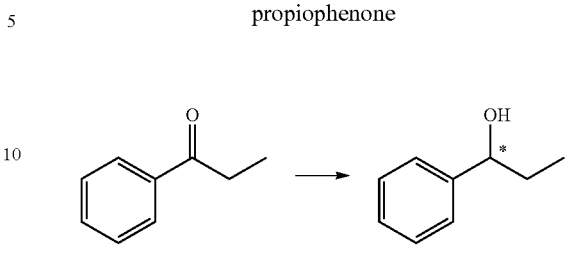

Dichloro(p-cymene)ruthenium(II) dimer (1.2 mg, 2 μmol, 0.5 mol %) and a chiral ligand (M=Ru, R=i-Pr, Ar=C₆H₅—, 2.6 μmol, 0.65 mol %) were dissolved in i-propanol (3 mL) under nitrogen atmosphere, and then heated and stirred for 1 h at 85° C. After the mixture was cooled to room temperature, propiophenone (0.4 mmol), i-propanol (2 mL) and a solution of sodium carbonate in i-propanol (0.4 mL, 0.2 M) were added thereto. Thereafter, the reaction system was placed in an autoclave, and stirred for 24 h under $H_2$ (5 atm) at 10° C. The solvent was removed under reduced pressure, and the resultants were separated by column chromatography (silica gel column; eluent:ethyl acetate/petroleum ether=1/8). Accordingly, pure 1-phenylpropanol was obtained and the ee value (ee=99.2%) was measured by GC analysis.

Example 31

Preparation of 1-phenylbutynol from 1-phenylbutan-1-one

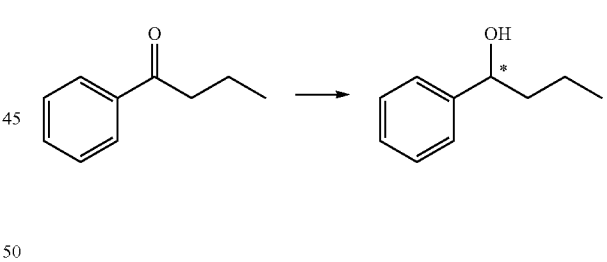

Benzeneruthenium(II) chloride dimer (1.0 mg, 2 μmol, 0.5 mol %) and a chiral ligand (M=Ru, R=t-Bu, Ar=3,5-t-Bu₂C₆H₃—, 2.6 μmol, 0.65 mol %) were dissolved in i-propanol (3 mL) under nitrogen atmosphere, and then heated and stirred for 1 h at 85° C. After the mixture was cooled to room temperature, 1-phenylbutan-1-one (0.4 mmol), i-propanol (2 mL) and a solution of sodium hydroxide in i-propanol (0.4 mL, 0.4 M) were added thereto. Thereafter, the reaction system were placed in an autoclave, and stirred for 12 h under $H_2$ (10 atm) at 40° C. The solvent was removed under reduced pressure, and the resultants were separated by column chromatography (silica gel column; eluent:ethyl acetate/petroleum ether=1/8). Accordingly, pure 1-phenylbutynol was obtained and the ee value (ee=99.2%) was measured by GC analysis.

Example 32

Preparation of 2-methyl-1-phenyl-1-propanol from i-butyrophenone

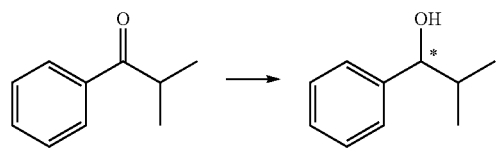

Benzeneruthenium(II) chloride dimer (1.0 mg, 2 μmol, 0.5 mol %) and a chiral ligand (M=Fe, R=i-Pr, Ar=4-MeC$_6$H$_4$—, 2.6 μmol, 0.65 mol %) were dissolved in xylene (3 mL) under nitrogen atmosphere, and then heated and stirred for 1 h at 140° C. After the mixture was cooled to room temperature, i-butyrophenone (0.4 mmol), xylene (2 mL) and a solution of sodium carbonate in i-propanol (0.4 mL, 0.2 M) were added thereto. Thereafter, the reaction system was placed in an autoclave, and stirred for 12 h under H$_2$ (5 atm) at 40° C. The solvent was removed under reduced pressure, and the resultants were separated by column chromatography (silica gel column; eluent: ethyl acetate/petroleum ether=1/5). Accordingly, pure 2-methyl-1-phenyl-1-propanol was obtained and the ee value (ee=99.3%) was measured by GC analysis.

Example 33

Preparation of 1-phenylpentanol from pentanophenone

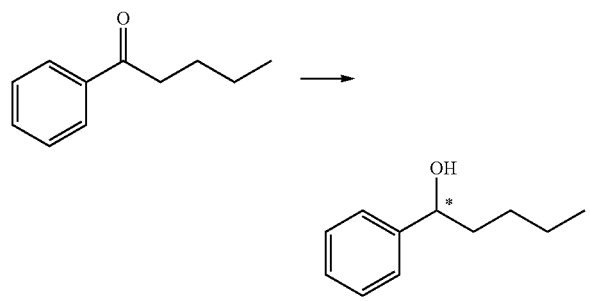

Tris(triphenylphosphine)ruthenium (II) chloride (1.9 mg, 2 μmol, 0.5 mol %) and a chiral ligand (M=Ru, R=i-Pr, Ar=C$_6$H$_5$—, 1.3 μmol, 0.33 mol %) were dissolved in xylene (3 mL) under nitrogen atmosphere, and then heated and stirred for 1 h at 140° C. After the mixture was cooled to room temperature, pentanophenone (0.4 mmol), xylene (2 mL) and a solution of potassium hydroxide in methanol (0.4 mL, 0.2 M) were added thereto. Thereafter, the reaction system was placed in an autoclave, and stirred for 12 h under H$_2$ (10 atm) at 25° C. The solvent was removed under reduced pressure, and the resultants were separated by column chromatography (silica gel column; eluent:ethyl acetate/petroleum ether=1/8). Accordingly, pure 1-phenylpentanol was obtained and the ee value (ee=99.6%) was measured by GC analysis.

Example 34

Preparation of 1-(p-methylphenyl)octanol from p-methyloctanophenone

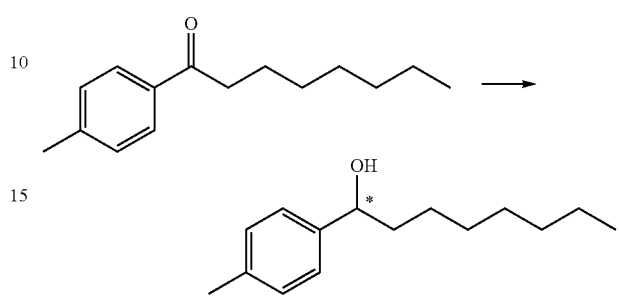

Tris(triphenylphosphine)ruthenium (II) chloride (1.9 mg, 2 μmol, 0.5 mol %) and a chiral ligand (M=Ru, R=t-Bu, Ar=C$_6$H$_5$—, 1.3 μmol, 0.33 mol %) were dissolved in xylene (3 mL) under nitrogen atmosphere, and then heated and stirred for 2 h at 140° C. After the mixture was cooled to room temperature, p-methyloctanophenone (0.8 mmol), xylene (2 mL) and a solution of potassium hydroxide in methanol (0.8 mL, 0.2 M) were added thereto. Thereafter, the reaction system was placed in an autoclave, and stirred for 6 h under H$_2$ (10 atm) at 50° C. The solvent was removed under reduced pressure, and the resultants were separated by column chromatography (silica gel column; eluent:ethyl acetate/petroleum ether=1/5). Accordingly, pure 1-(p-methylphenyl)octanol was obtained and the ee value (ee=99.0%) was measured by GC analysis.

Example 35

Preparation of 3-(1-hydroxyethyl)pyridine from 3-acetylpyridine

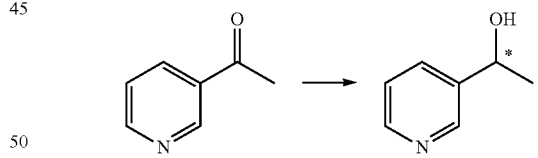

Tris(triphenylphosphine)ruthenium(II) chloride (3.8 mg, 4 μmol, 1 mol %) and a chiral ligand (M=Ru, R=t-Bu, Ar=C$_6$H$_5$—, 2.6 μmol, 0.65 mol %) were dissolved in tetrahydrofuran (3 mL) under nitrogen atmosphere, and then heated and stirred for 2 h at 65° C. After the mixture was cooled to room temperature, 3-acetylpyridine (0.4 mmol), tetrahydrofuran (2 mL) and a solution of potassium ethoxide in ethanol (0.1 mL, 0.2M) were added thereto. Thereafter, the reaction system was placed in an autoclave, and stirred for 6 h under H$_2$ (50 atm) at 25° C. The solvent was removed under reduced pressure, and the resultants were separated by column chromatography (silica gel column; eluent:ethyl acetate/ petroleum ether=1/1). Accordingly, pure 3-(1-hydroxyethyl) pyridine was obtained and the ee value (ee=93%) was measured by GC analysis.

Example 36

Preparation of 2-(1-hydroxyethyl)furan from 2-acetylfuran

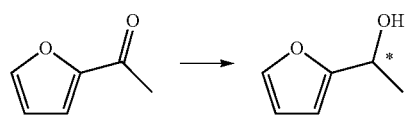

Benzeneruthenium(II) chloride dimer (1.0 mg, 2 µmol, 0.1 mol %) and a chiral ligand (M=Fe, R=t-Bu, Ar=4-MeOC$_6$H$_4$—, 2.6 µmol, 0.13 mol %) were dissolved in i-propanol (15 mL) under nitrogen atmosphere, and then heated and stirred for 0.5 h at 85° C. After the mixture was cooled to room temperature, 2-acetylfuran (2.0 mmol), i-propanol (15 mL) and a solution of potassium methoxide in i-propanol (2.0 mL, 0.2 M) were added thereto. Thereafter, the reaction system was placed in an autoclave, and stirred for 48 h under H$_2$ (40 atm) at −20° C. The solvent was removed under reduced pressure, and the resultants were separated by column chromatography (silica gel column; eluent:ethyl acetate/petroleum ether=1/5). Accordingly, pure 2-(1-hydroxyethyl)furan was obtained and the ee value (ee=98%) was measured by GC analysis.

Example 37

Preparation of 1,2,3,4-tetrahydro-1-naphthol from 1-tetralone

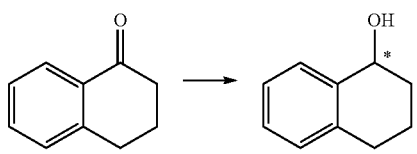 [SMILES: O=C1CCCc2ccccc21 ; OC1CCCc2ccccc21]

Tris(triphenylphosphine)ruthenium (II) chloride (1.9 mg, 2 µmol, 0.5 mol %) and a chiral ligand (M=Ru, R=i-Pr, Ar=C$_6$H$_5$—, 1.3 µmol, 0.33 mol %) were dissolved in ethanol (3 mL) under nitrogen atmosphere, and then heated and stirred for 1 h at 80° C. After the mixture was cooled to room temperature, 1-tetralone (0.4 mmol), ethanol (2 mL) and a solution of potassium hydroxide in ethanol (0.4 mL, 0.2 M) were added thereto. Thereafter, the reaction system was placed in an autoclave, and stirred for 48 h under H$_2$ (10 atm) at 0° C. The solvent was removed under reduced pressure, and the resultants were separated by column chromatography (silica gel column; eluent: ethyl acetate/petroleum ether=1/5). Accordingly, pure 1,2,3,4-tetrahydro-1-naphthol was obtained and the ee value (ee=99.7%) was measured by GC analysis.

Example 38

Preparation of 1-hydroxylhydrindene from 1-indanone

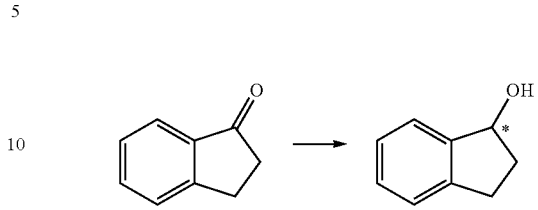

Tris(triphenylphosphine)ruthenium (II) chloride (0.76 mg, 0.8 µmol, 0.2 mol %) and a chiral ligand (M=Ru, R=i-Pr, Ar=C$_6$H$_5$—, 0.52 µmol, 0.13 mol %) were dissolved in ether (3 mL) under nitrogen atmosphere, and then heated and stirred for 2 h at 40° C. After the mixture was cooled to room temperature, 1-indanone (0.4 mmol), ether (2 mL) and an aqueous solution of potassium carbonate (0.2 mL, 0.2 M) were added thereto. Thereafter, the reaction system was placed in an autoclave, and stirred for 12 h under H$_2$ (5 atm) at 25° C. The solvent was removed under reduced pressure, and the resultants were separated by column chromatography (silica gel column; eluent: ethyl acetate/petroleum ether=1/5). Accordingly, pure 1-hydroxylhydrindene was obtained and the ee value (ee=99.5%) was measured by GC analysis.

The invention claimed is:

1. An asymmetric hydrogenation method for ketone compounds, comprising the step of:
    under hydrogen atmosphere with a hydrogen pressure of 3~50 atm, in the presence of an in situ catalyst derived from a chiral ligand and a ruthenium salt, adding a ketone compound and a base into a second solvent to carry out an asymmetric hydrogenation for the ketone compound;
    wherein the chiral ligand is a compound of formula (IV):

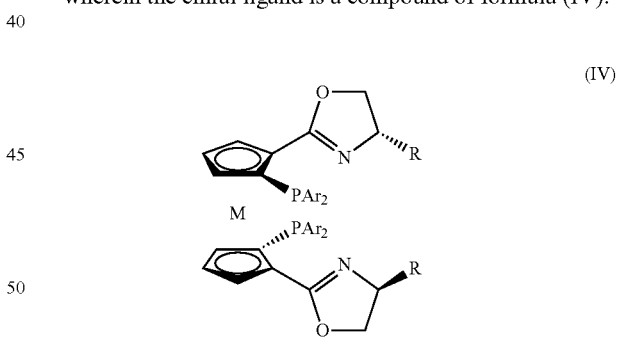

(IV)

in formula (IV), M represents iron or ruthenium; R represents methyl, C$_2$-C$_8$ saturated aliphatic group, phenyl or benzyl; Ar represents substituted or unsubstituted aromatic group;
   wherein the in situ catalyst is obtained by reacting the chiral ligand with the ruthenium salt in a first solvent;
   wherein when the chiral ligand reacts with the ruthenium salt in the first solvent to produce the in situ catalyst, the molar ratio of ruthenium derived from the ruthenium salt to the chiral ligand is 1:0.5~0.7.

2. The asymmetric hydrogenation method for ketone compounds according to claim 1, wherein in formula (IV), M represents iron or ruthenium; R represents methyl, ethyl, n-propyl, i-propyl, n-butyl, s-butyl, t-butyl, pentyl, phenyl or benzyl; Ar represents phenyl, p-methylphenyl, p-methoxyphenyl, 3,5-dimethylphenyl, 3,5-di-t-butylphenyl, 3,5-di(trifluoromethyl)phenyl.

3. The asymmetric hydrogenation method for ketone compounds according to claim 1, wherein the ruthenium salt is any one selected from tris(triphenylphosphine) ruthenium(II) chloride, benzeneruthenium(II) chloride dimer, or dichloro(p-cymene)ruthenium(II) dimer.

4. The asymmetric hydrogenation method for ketone compounds according to claim 1, wherein the first solvent is any one selected from methanol, ethanol, i-propanol, dichloromethane, 1,4-dioxane, tetrahydrofuran, diethyl ether, toluene, or xylene.

5. The asymmetric hydrogenation method for ketone compounds according to claim 1, wherein when the chiral ligand reacts with the ruthenium salt in the first solvent to produce the in situ catalyst, the reaction temperature is 30° C.~140° C. and the reaction time is 0.5 h~3 h.

6. The asymmetric hydrogenation method for ketone compounds according to claim 1, wherein the second solvent is any one selected from methanol, ethanol, i-propanol, dichloromethane, 1,4-dioxane, tetrahydrofuran, diethyl ether, toluene, or xylene.

7. The asymmetric hydrogenation method for ketone compounds according to claim 1, wherein the ketone compound is a compound of formulae (I), (II), or (III):

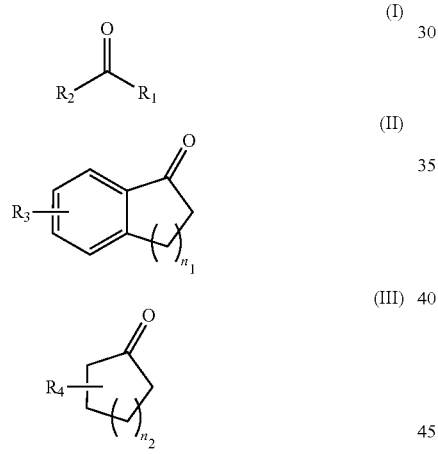

in formula (I), $R_1$ represents $C_1$-$C_{15}$ linear or branched alkyl or alkenyl, or $C_3$-$C_{15}$ saturated cyclic hydrocarbyl; $R_2$ represents $C_4$-$C_{20}$ substituted or unsubstituted aromatic group or aromatic heterocyclic group, or $C_1$-$C_{15}$ linear or branched alkyl or alkenyl, or $C_3$-$C_{15}$ saturated cyclic hydrocarbyl;

in formula (II), $R_3$ represents —$OR_5$, —$NHR_6$, —F, —Cl, —Br, —I, —$NO_2$, —OH, $C_1$-$C_{15}$ linear or branched alkyl or alkenyl, or $C_3$-$C_{15}$ saturated cyclic hydrocarbyl; $n_1$ is an integer from 0 to 4; $R_5$ and $R_6$ independently represent $C_1$-$C_{15}$ linear or branched alkyl or alkenyl, or $C_3$-$C_{15}$ saturated cyclic hydrocarbyl;

in formula (III), $R_4$ represents —$OR_7$, —$NHR_8$, —F, —Cl, —Br, —I, —$NO_2$, —OH, $C_1$-$C_{15}$ linear or branched alkyl or alkenyl, or $C_3$-$C_{15}$ saturated cyclic hydrocarbyl; $n_2$ is an integer from 0 to 4; $R_7$ and $R_8$ independently represent $C_1$-$C_{15}$ linear or branched alkyl or alkenyl, or $C_3$-$C_{15}$ saturated cyclic hydrocarbyl.

8. The asymmetric hydrogenation method for ketone compounds according to claim 1, wherein the base is any one selected from potassium t-butoxide, sodium t-butoxide, sodium ethoxide, potassium ethoxide, sodium methoxide, potassium methoxide, potassium hydroxide, sodium hydroxide, potassium carbonate, sodium carbonate, potassium bicarbonate, or sodium bicarbonate.

9. The asymmetric hydrogenation method for ketone compounds according to claim 1, wherein the molar ratio of the base to the ketone compound is 0.2~0.02:1.

10. The asymmetric hydrogenation method for ketone compounds according to claim 1, wherein when the ketone compound undergoes the asymmetric hydrogenation, the reaction temperature is −20~50° C., and the reaction time is 6~72 h.

11. The asymmetric hydrogenation method for ketone compounds according to claim 1, comprising the following first and second steps:
in the first step, reacting the chiral ligand with the ruthenium salt in the first solvent to obtain the in situ catalyst;
in the second step, under hydrogen atmosphere, in the presence of the in situ catalyst obtained from the chiral ligand and the ruthenium salt, the ketone compound and the base are added into the second solvent to carry out the asymmetric hydrogenation for the ketone compound; and the first and second steps are continuously performed without additional separation of the in situ catalyst obtained in the first step.

* * * * *